United States Patent
De Man et al.

(10) Patent No.: US 11,039,805 B2
(45) Date of Patent: Jun. 22, 2021

(54) DEEP LEARNING BASED ESTIMATION OF DATA FOR USE IN TOMOGRAPHIC RECONSTRUCTION

(71) Applicant: General Electric Company, Schenectady, NY (US)

(72) Inventors: Bruno Kristiaan Bernard De Man, Niskayuna, NY (US); Bernhard Erich Hermann Claus, Niskayuna, NY (US); Jiang Hsieh, Waukesha, WI (US); Yannan Jin, Niskayuna, NY (US); Zhanfeng Xing, Beijing (CN)

(73) Assignee: General Electric Company, Schenectady, NY (US)

( * ) Notice: Subject to any disclaimer, the term of this patent is extended or adjusted under 35 U.S.C. 154(b) by 72 days.

(21) Appl. No.: 16/474,861

(22) PCT Filed: Jan. 5, 2017

(86) PCT No.: PCT/CN2017/070283
§ 371 (c)(1),
(2) Date: Jun. 28, 2019

(87) PCT Pub. No.: WO2018/126396
PCT Pub. Date: Jul. 12, 2018

(65) Prior Publication Data
US 2019/0328348 A1 Oct. 31, 2019

(51) Int. Cl.
*G06K 9/00* (2006.01)
*A61B 6/00* (2006.01)
(Continued)

(52) U.S. Cl.
CPC ......... *A61B 6/5205* (2013.01); *G06N 3/0454* (2013.01); *G06N 3/08* (2013.01);
(Continued)

(58) Field of Classification Search
CPC ....... A61B 6/5205; A61B 6/032; A61B 6/037; A61B 6/5258; A61B 6/03;
(Continued)

(56) References Cited

U.S. PATENT DOCUMENTS 5,732,697 A 3/1998 Zhang
10,762,687 B2 * 9/2020 Westerhoff ............. G16H 50/70
(Continued)

FOREIGN PATENT DOCUMENTS

| CN | 103646410 | * | 3/2014 | ............. G06T 11/00 |
| JP | 2007201572 A | | 8/2007 | |
| WO | 20151486161 W | | 10/2015 | |

OTHER PUBLICATIONS

U.S. Appl. No. 62/354,319, filed Jun. 24, 2016. (Year: 2016).*
(Continued)

*Primary Examiner* — Jose L Couso

(57) ABSTRACT

A method relates to the use of deep learning techniques, which may be implemented using trained neural networks (50), to estimate various types of missing projection or other unreconstructed data. Similarly, the method may also be employed to replace or correct corrupted or erroneous projection data as opposed to estimating missing projection data.

17 Claims, 11 Drawing Sheets

(51) Int. Cl.
  *G06N 20/20* (2019.01)
  *G06N 3/04* (2006.01)
  *G06N 3/08* (2006.01)
  *G06T 3/40* (2006.01)
  *G06T 5/00* (2006.01)
  *G06T 5/20* (2006.01)
  *G06T 5/40* (2006.01)
  *G06T 5/50* (2006.01)
  *G06T 7/00* (2017.01)
  *G06T 11/00* (2006.01)

(52) U.S. Cl.
  CPC ........... *G06N 20/20* (2019.01); *G06T 3/4007* (2013.01); *G06T 5/002* (2013.01); *G06T 5/20* (2013.01); *G06T 5/40* (2013.01); *G06T 5/50* (2013.01); *G06T 7/0012* (2013.01); *G06T 11/008* (2013.01); *G06T 2207/10081* (2013.01); *G06T 2207/20081* (2013.01); *G06T 2207/20084* (2013.01); *G06T 2207/20224* (2013.01); *G06T 2211/432* (2013.01)

(58) Field of Classification Search
  CPC . A61B 2090/3762; A61B 5/00; A61B 5/0035; A61B 5/0073; A61B 5/7264; G01N 23/046; G01N 2223/419; G06N 20/20; G06N 20/00; G06N 20/10; G06N 3/0454; G06N 3/08; G06N 3/0472; G06N 3/084; G06N 3/0445; G06N 3/06; G06N 7/005; G06N 5/003; G06T 3/4007; G06T 3/4046; G06T 5/002; G06T 5/20; G06T 5/40; G06T 5/50; G06T 7/0012; G06T 11/008; G06T 11/005; G06T 11/006; G06T 11/003; G06T 2207/10081; G06T 2207/20081; G06T 2207/20084; G06T 2207/20224; G06T 2207/10104; G06T 2207/10108; G06T 2207/10088; G06T 2207/30004; G06T 2207/10072; G06T 2207/10076; G06T 2210/41; G06T 2211/432; G06T 2211/424; G06T 2211/421; G06T 2211/412; G06T 2211/416; G06F 19/321; G06F 19/00; G06F 17/11; G16H 30/40; G16H 30/20; G16H 50/50; G16H 50/20; G06K 2209/05; G06K 9/66; G06K 9/40; G06K 9/6231; G06K 9/6256; G06K 9/6298; Y10S 378/901

See application file for complete search history.

(56) References Cited

U.S. PATENT DOCUMENTS

| | | | |
|---|---|---|---|
| 2004/0264626 A1* | 12/2004 | Besson | A61B 6/563 378/4 |
| 2007/0253523 A1 | 11/2007 | Zamyatin | |
| 2011/0142301 A1 | 6/2011 | Boroczky | |
| 2015/0154765 A1* | 6/2015 | Huo | G06T 7/12 382/132 |
| 2016/0324499 A1 | 11/2016 | Sen Sharma | |
| 2017/0176609 A1 | 6/2017 | Tsubota | |
| 2017/0178365 A1* | 6/2017 | Raupach | G06T 7/11 |
| 2017/0362585 A1* | 12/2017 | Wang | G06N 3/08 |
| 2018/0350113 A1 | 12/2018 | Goto | |
| 2019/0325621 A1* | 10/2019 | Wang | G06N 3/084 |

OTHER PUBLICATIONS

Japanese Application No. 2019-536278 filed Jan. 5, 2017—Notice of Preliminary Rejection dated Jan. 12, 2021; 12 pages.
Gjesteby, Lars, et al. "Metal artifact reduction in CT: where are we after four decades." Ieee Access 4 (2016).
KR patent application 10-2019-7021386 filed Jul. 22, 2019; Office Action dated Sep. 28, 2020; 7 pages.
Nuyts, et al. "Modelling the physics in the iterative reconstruction for transmission computed tomography." Physics in Medicine and Biology 58.12 (2013).
Wang, Ge. "A perspective on deep imaging." IEEE access 4 (2016).

\* cited by examiner

DEEP LEARNING BASED ESTIMATION OF DATA FOR USE IN TOMOGRAPHIC RECONSTRUCTION

BACKGROUND

The subject matter disclosed herein relates to tomographic reconstruction, and in particular to the use of deep learning techniques to estimate missing, corrupt, or noisy data in the reconstruction process.

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through the target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

By way of example, various imaging modalities, such as X-ray-based computed tomography (CT) (e.g., multi-slice CT) and X-ray C-arm systems (e.g., cone-beam CT), measure projection data of an object or patient from various angles or views about the object or patient. The projection data corresponds to a Radon transform, fan-beam transform, or cone-beam transform. Using tomographic reconstruction techniques, cross-sectional images or volumetric images can be estimated or "reconstructed" from the projection data. For example, in the case of CT, cross-sectional images may be reconstructed from the projection data (i.e., Radon transform data).

For various reasons, a portion of the projection data can be corrupt or missing (relative to an ideal or mathematically complete projection dataset) for a given examination, which can lead to image artifacts. Traditional interpolation techniques, extrapolation techniques, or iterative estimation techniques do not always adequately address such instances of missing or incomplete data and, in some cases, can be slow to compute.

BRIEF DESCRIPTION

In one embodiment, a method for estimating missing data for use in a tomographic reconstruction is provided. In accordance with this method, a set of scan data is acquired or accessed. The set of scan data has one or more regions of incomplete or unsuitable data. The set of scan data is processed using one or more trained neural networks. An estimated data set for each region of incomplete or unsuitable data is generated using the one or more trained neural networks. The set of scan data in combination with the estimated data sets correspond to a corrected set of scan data. A tomographic reconstruction of the corrected set of scan data is performed to generate one or more reconstructed images.

In a further embodiment, an image processing system is provided. In accordance with this embodiment, the image processing system includes: a processing component configured to execute one or more stored processor-executable routines; and a memory storing the one or more executable routines. The one or more executable routines, when executed by the processing component, cause acts to be performed comprising: acquiring or accessing a set of scan data, wherein the set of scan data has one or more regions of incomplete or unsuitable data; processing the set of scan data using one or more trained neural networks; generating an estimated data set for each region of incomplete or unsuitable data using the one or more trained neural networks, wherein the set of scan data in combination with the estimated data sets correspond to a corrected set of scan data; performing a tomographic reconstruction of the corrected set of scan data to generate one or more reconstructed images.

In another embodiment, a neural network training method is provided. In accordance with this method, a plurality of sets of complete scan data are acquired or accessed. The sets of complete scan data are measured or simulated. One or more regions within each set of complete scan data are marked as target output regions. One or more regions of each set of complete scan data not marked as a target output region are available as known data regions. A neural network is trained to generate a trained neural network by providing the scan data for the known regions and corresponding scan data for the target output regions for each set of complete scan data to the neural network.

In one embodiment, a neural network training method is provided. In accordance with this method, a plurality of sets of scan data are acquired or accessed. One or more image quality metrics are generated or acquired for one or more target regions of each set of scan data and one or more input regions of each set of scan data. A neural network is trained to generate a trained neural network by providing the sets of scan data, the image quality metrics for the target regions for each set of scan data, and the image quality metrics of the input regions for each set of scan data to the neural network.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
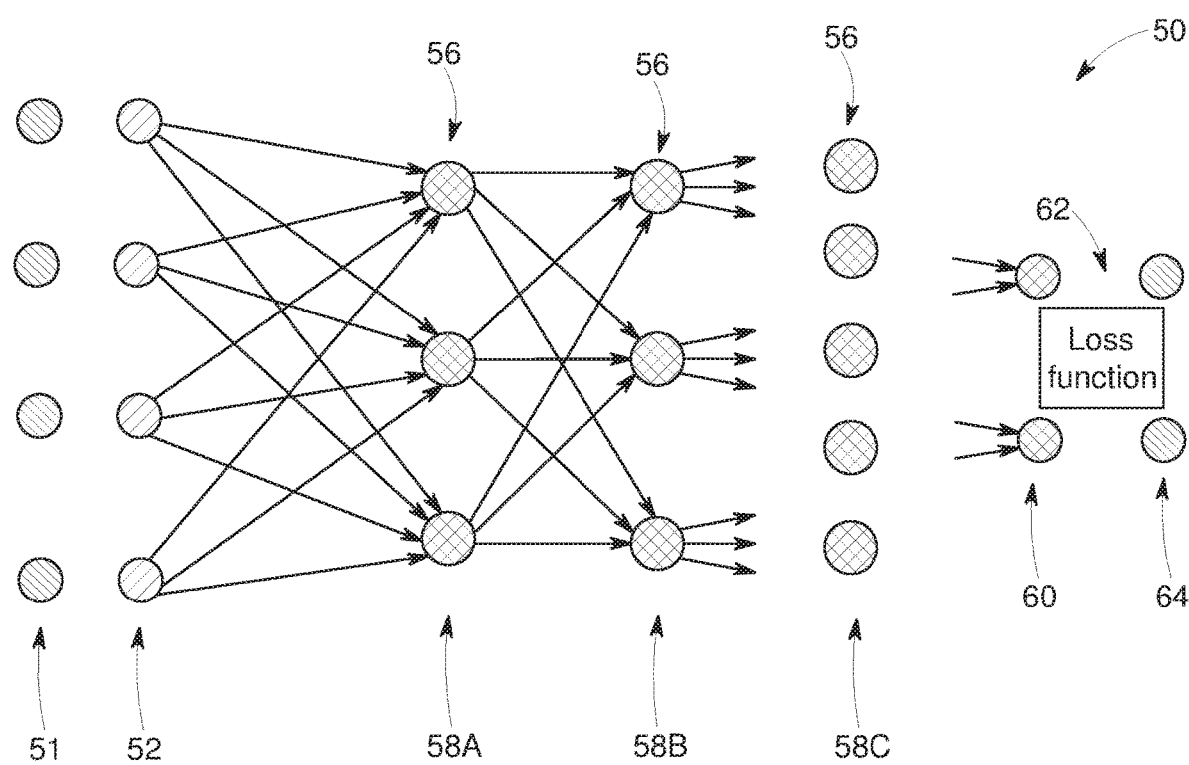
FIG. 1 depicts an example of an artificial neural network for training a deep learning model, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

While aspects of the following discussion are provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as the tomographic image reconstruction for industrial Computed Tomography (CT) used in non-destructive inspection of manufactured parts or goods (i.e., quality control or quality review applications), and/or the non-invasive inspection of packages, boxes, luggage, and so forth (i.e., security or screening applications). In general, the present approaches may be desirable in any imaging or screening context or image processing field where a set or type of acquired data undergoes a reconstruction process to generate an image or volume and where the acquired data may be subject to omission, noise, or corruption that would otherwise impact the reconstructed image(s).

Though CT examples are primarily provided herein, it should be understood that the present approach may be used in other imaging modality contexts where incomplete, corrupt, or noisy data may impact downstream tomographic reconstruction processes or the resulting images. For instance, the presently described approach may also be suitable for use with other types of tomographic scanners including, but not limited to, reconstruction using positron emission tomography (PET), single photon emission computed tomography (SPECT), phase-contrast imaging, and/or magnetic resonance imaging (MRI).

Within the CT context (and as may have corollaries in the other imaging modalities mentioned) a sinogram is a canonical representation of axial projection data where the measured data is arranged in a 2D configuration where one axis corresponds to the projection/view angle, and the other axis corresponds to the spatial offset essentially perpendicular to the projection/view angle. For example, in a fan-beam CT acquisition, the first axis corresponds to the gantry angle and the second axis corresponds to the angle of the ray within the fan (or, equivalently, the position of the pixel within the detector array). Thus, in this 2D context a region of missing data, as may be referenced herein, refers to one or more contiguous regions in this sinogram domain for which measurements are incomplete, are corrupt, and/or are otherwise not of the same quality. Although the present discussion is focused on examples in a 2D context, both for simplicity and to facilitate explanation, the present approaches may also be implemented in a 3D context (e.g., cone-beam CT), where the third axis represents the azimuthal angle, i.e., the angle of the projection ray with respect to the axial plane). Thus, in such 3D implementations, the projection data has 3 dimensions: a rotation angle (view number), a detector column (transaxially), and a detector row (longitudinally). In such a context, patches or traces of missing data can be three-dimensional and neighboring patches or traces of available or known data can be three-dimensional and the extrapolation of the present concepts to the third dimension should be apparent to those skilled in the art.

As noted herein, for various reasons a portion of the projection (or other) data acquired for tomographic reconstruction (e.g., reconstruction of cross-sectional or volumetric images) can be corrupt or missing, which can lead to artifacts in the reconstructed images. Examples of causes of missing projection data include, but are not limited to: (1) metal objects or high-density objects in the imaged volume—due to the high attenuation and associated physical effects, projection data in the shadow of the metal objects can be corrupted and considered 'missing'; (2) transaxial truncation—when the imaged object or patient extends outside of the scan field-of-view, the projections are said to be truncated, i.e., some projection data that is needed for a good reconstruction is missing; (3) longitudinal truncation—in cone-beam reconstruction, a portion of the reconstructed volume is not measured or is insufficiently sampled due to the finite number of detector rows; and (4) bad detector pixels or gaps between detector modules—individual or groups of detector pixels may not operate reliably and the data is considered missing. Similarly, there can be gaps between detector modules or panels, leading to missing data.

To address issues related to missing or incomplete projection data, the present approach employs deep learning techniques, such as in the form of trained neural networks, to estimate various types of missing projection data. The neural networks can be trained using projection data where a portion of the data is defined as the missing data to be estimated and the remaining data is the available data that can be used as the input to the network. Similarly, the present approach may also be employed to replace or correct corrupted or erroneous projection data (as opposed to estimating missing projection data). For example, more general data errors (such as due to beam hardening, scatter, noise, and so forth) may be addressed by this approach using a trained neural network and the methodology generally described herein. In such instances, instead of estimating missing projection data, one or more correction terms may be estimated that may be employed to correct the incorrect data. Alternatively, corrected projection data may be estimated directly, which will then replace the corrupted projection data.

With the preceding introductory comments in mind, the approaches described herein utilize deep learning techniques to estimate missing data used in tomographic reconstruction processes, such as the reconstruction processes used to generate CT, PET, SPECT, or MR images. As discussed herein, deep learning techniques (which may also be known as deep machine learning, hierarchical learning, or deep structured learning) are a branch of machine learning techniques that employ mathematical representations of data and artificial neural networks for learning. By way of example, deep learning approaches may be characterized by their use of one or more network architectures to extract or model high level abstractions of a type of data of interest. This may be accomplished using one or more processing layers, where the number and configuration of the layers allows the networks to address complex information extraction and modeling tasks. The specific parameters of the network (in some contexts referred to as "weights" and "biases") are typically estimated through a so-called learning process; although in some embodiments the learning process itself may also extend to learning elements of the network architecture. The estimated/learned parameters typically result in a network where each layer corresponds to a different level of abstraction and, therefore potentially extracts or models different aspects of the initial data or outputs of a preceding layer, i.e., such a network may often represent a hierarchy or cascade of layers. In an image processing or reconstruction context, this may sometimes be characterized as different layers corresponding to the different feature levels or resolution in the data. Processing may therefore proceed hierarchically, i.e., earlier or higher level layers may correspond to extracting "simple" features from the input data, followed by layers that combine these simple features into features exhibiting higher level of complexity. In practice, each layer (or, more specifically, each "neuron" in each layer) may employ one or more linear and/or non-linear transforms (the so-called activation functions) to process the input data to an output data representation for the layer.

As discussed herein, as part of the initial training of deep learning processes to solve a particular problem, training data sets may be employed that have known input values (e.g., input images or input projection data values) and known or desired values for one or both of the final output (e.g., target images or projection data values) of the deep learning process or for individual layers of the deep learning process (assuming a multi-layer network architecture). In this manner, the deep learning algorithms may process (either in a supervised or guided manner or in an unsupervised or unguided manner) the known or training data sets until the mathematical relationships between the initial data and desired output(s) are discerned and/or the mathematical relationships between the inputs and outputs of each layer are discerned and characterized. The learning process typically utilizes (part of) the input data and creates a network output for this input data. The created output is then compared to the desired (target) output for this data set, and the difference between the generated and the desired output is then used to iteratively update the parameters (weights and biases) of the network. One such update/learning mechanism uses a stochastic gradient descent (SGD) approach for updating the parameters of the network; other methods known in the art may be used as well. Similarly, separate validation data sets may be employed in which both input and desired target values are known, but only the initial values are supplied to the trained deep learning algorithms, with the outputs then being compared to the outputs of the deep learning algorithm to validate the prior training and/or to prevent over-training.

By way of visualization, FIG. 1 schematically depicts an example of an artificial neural network 50 that may be trained as a deep learning model or network as discussed herein. In this example, the network 50 is multi-layered, with input data 51 received or acquired by an input layer 52 and multiple layers including hidden layers 58A, 58B, 58C and so forth, and an output layer 60 and the training target 64 present in the network 50. Each layer, in this example, is composed of a plurality of "neurons" 56. The number of neurons 56 may be constant between layers or, as depicted, may vary from layer to layer. Neurons 56 at each layer generate respective outputs that serve as inputs to the neurons 56 of the next hierarchical layer. In practice, a weighted sum of the inputs with an added bias is computed to "excite" or "activate" each respective neuron of the layers according to an activation function, such as a sigmoid activation function, or a rectified linear unit (ReLU) or otherwise specified or programmed. In the present context, the outputs of the final layer constitute the network output 60 (e.g., predicted projection data) which, in conjunction with target projection data values 64, are used to compute some loss or error function 62, which will be backpropagated to guide the network training (using SGD, or other approaches). As discussed herein, in certain projection-based contexts the output 60 of the neural network 50 may be one or more of a single projection data number (i.e., a single missing or corrected projection value), a projection data patch, or a trace of projection data. While FIG. 1 depicts a simple fully connected network, with a clear layer-by-layer architecture, other architectures may be selected for individual layers, a combination of multiple layers, or the full network. For example, one or more layers may be represented by a convolutional neural network (CNN), or other architecture. Similarly, some parts of the network may utilize a hybrid architecture that is not configured according to a strictly sequential layer-by-layer processing architecture. For example, some connections may skip one or more layers (i.e., directly connect nodes residing in layers which are not consecutive); or a network architecture may be selected that does not correspond to a clear layer-by-layer architecture.

The loss or error function 62 measures the difference between the network output (i.e., predicted projection data values) and the corresponding training target (i.e., actual or ground truth projection data values). In certain implementations, the loss function may be a mean squared error (MSE) and/or may account for differences involving other image or projection data features. Alternatively, the loss function 62 could be defined by other metrics associated with the particular task in question.

In one embodiment, while the configuration of the neural network 50 will be guided by prior knowledge of the estimation problem, dimensionality of inputs, outputs, etc., the learning itself is treated as "black-box", and relies primarily or exclusively on achieving the best approximation of the desired output data 60 as a function of the input data. In such a scenario, the fact that certain neurons 56 in the network 50 may correspond to certain features in the data is owed to the learning process, which typically converges naturally to such a solution. In various alternative implementations, certain aspects and/or characteristics of the data, imaging geometry, reconstruction algorithm, and so forth can be leveraged to give an explicit meaning to certain data representations in the neural network 50. This may be helpful to speed up training, since this creates an opportunity to separately train (or pre-train) or define certain layers in the neural network 50.

For example, based on the knowledge that the ramp-filter in a filtered backprojection reconstruction algorithm is sensitive to the derivative of the data (within each projection image), the initial layer(s) of the neural network 50 may be pre-trained to represent the derivative of missing projection data, as discussed herein; while the subsequent layer(s) may be used to reconstruct or estimate the missing data itself from the derivative.

The input data and/or the target data may also undergo a pre-processing step such that one or both are converted to a domain where the missing data is easier to estimate. After the missing data is estimated, a post-processing step that is the inverse of the pre-processing step may be applied to obtain the final estimated data. For example, a one-dimensional or multi-dimensional high-pass filter may be applied as a pre-processing step to emphasize high frequencies. After deep learning estimation of the missing data, a one-dimensional or multi-dimensional low-pass filter may be applied to compensate for the effect of the high-pass filter.

In a similar embodiment, the sinogram may be normalized by dividing by or subtracting a reprojected sinogram prior to applying the proposed deep learning estimation technique. After the deep learning estimation, this normalization can be undone, by multiplying by or adding the same reprojected sinogram. The reprojected sinogram may be obtained as the reprojection of an initial reconstruction, where the initial reconstruction may be obtained using a standard type of metal artifact reduction. In such an embodiment the purpose of the processing is not to directly estimate the missing data, but to improve on the results obtained by a method from the prior art, e.g., by estimating a correction term, or estimate corrected data based on the original data and the result from the prior method.

Finally, in addition to the input data, the neural network may also receive weight (or confidence) data as additional inputs. The weight data represent how reliable the input data is. For example, each element of the input data could have a corresponding element in the weight data. The portion of the input data that is more reliable—for example less noisy or corrupt—may have higher associated weight data. The portion of the input data that is less reliable—for example more noisy or corrupt—may have lower associated weight data.

Similarly, for certain data estimation approaches discussed herein (such as a trace-based estimation, discussed in greater detail below), the knowledge about the periodicity of the data (such as within traces corresponding to input data as well as in traces corresponding to data to be estimated, as discussed below) the Fourier transform of the data may be used for input and/or output. Additional or subsequent layers may optionally be used to implement/approximate a Fourier or inverse Fourier transform.

Further, for projection data estimation approaches as discussed herein, for increased robustness to noise a multi-scale approach may be used where coarse-scale projection data information is processed separately (in at least some layers) from fine-scale information. Combination of coarse and fine-scale features may again be a separate layer. That is, different layers of the neural network 50 may correspond to different levels of granularity or resolution, or combinations of such scales.

Similarly, some elements of the architecture of the neural network 50 may be configured, pre-trained, or trained, to leverage elements or aspects of the respective reconstruction approach. By way of example, in the context of limited angle reconstruction approaches (e.g., tomosynthesis) multi-scale processing may be combined with non-linear processing (e.g., using soft-thresholding to minimize streak artifacts), leading to a significant improvement in achieved image quality. Where features of the reconstruction approach like this can be identified, the network architecture may be configured and/or training may be performed to mimic or facilitate such reconstruction features. In such a manner, the missing data estimation step as performed by the neural network may be tightly integrated with the specific reconstruction process that is utilized to generate a 3D volumetric image from the processed projection data, where some aspects of the reconstruction process (e.g., multi-scale filtering, ramp-filtering, etc.) may already be performed by the processing as disclosed here. By way of example, intermediate layers of the neural network 50 may be configured or trained to represent or correspond to a required pre-processing (in some reconstruction approach) for a limited angle reconstruction of structures behind or in front of a metal (or other radiopaque) region, based on data from adjacent views within a small angular range of the considered view angle.

Furthermore, the first layer(s) of the neural network 50 can be configured or trained to consist essentially of analysis functions. For example, the output of the first layer may represent essentially the scalar product of the data inside the input patches with the analysis functions. Since the structure of the sinogram is understood, in one embodiment such analysis functions (i.e., functions that reflect the characteristics of the sinusoidal profiles that a sinogram consists of) can be constructed explicitly. In one such implementation, the training may be faster since the first layer of such a network 50 does not need to be learned/trained.

Note that in any of these scenarios, later stages of the training process may still be configured to update/modify parts of the network 50 that were previously pre-trained or explicitly modeled or selected, thereby further improving performance of the overall network.

To facilitate explanation of the present missing data estimation using deep learning techniques, the present disclosure primarily discusses these approaches in the context of a CT system. However, it should be understood that the following discussion may also be applicable to other image modalities and systems including, but not limited to, PET, SPECT, and MRI, as well as to non-medical contexts or any context where tomographic reconstruction steps may be employed to reconstruct an image from data sets that may be incomplete or otherwise missing data.

Figure 2:
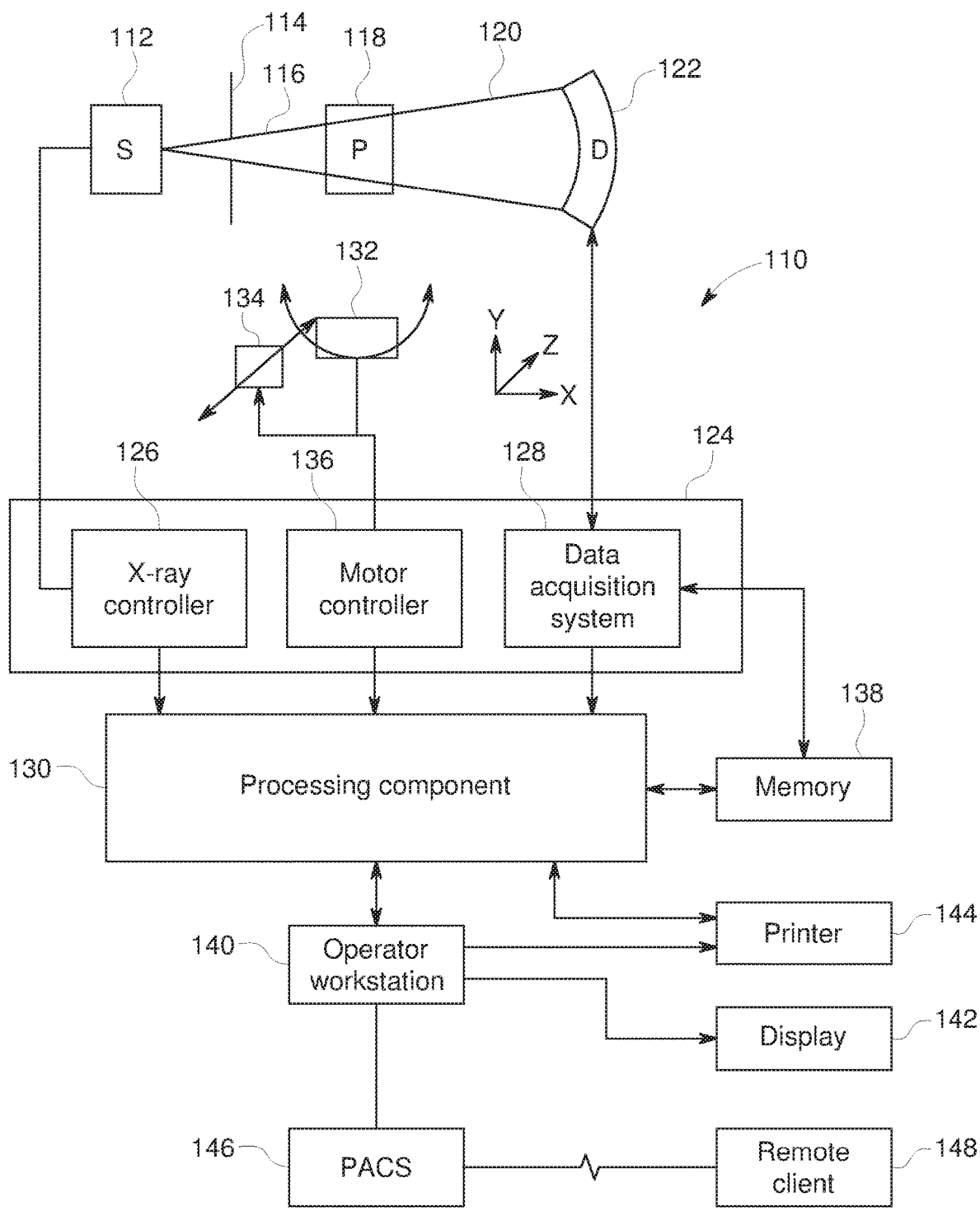
FIG. 2 is a block diagram depicting components of a computed tomography (CT) imaging system, in accordance with aspects of the present disclosure.

With this in mind, an example of an imaging system 110 (i.e., a scanner) is depicted in FIG. 2. In the depicted example, the imaging system 110 is a CT imaging system designed to acquire scan data (e.g., X-ray attenuation data) at a variety of views around a patient (or other subject or object of interest) and suitable for performing image reconstruction using data completion techniques as discussed herein. In the embodiment illustrated in FIG. 2, imaging system 110 includes a source of X-ray radiation 112 positioned adjacent to a collimator 114. The X-ray source 112 may be an X-ray tube, a distributed X-ray source (such as a solid-state or thermionic X-ray source) or any other source of X-ray radiation suitable for the acquisition of medical or other images.

In the depicted example, the collimator 114 shapes or limits a beam of X-rays 116 that passes into a region in which a patient/object 118, is positioned. In the depicted example, the X-rays 116 are collimated to be a cone-shaped beam, i.e., a cone-beam, that passes through the imaged volume. A portion of the X-ray radiation 120 passes through or around the patient/object 118 (or other subject of interest) and impacts a detector array, represented generally at reference numeral 122. Detector elements of the array produce electrical signals that represent the intensity of the incident X-rays 120. These signals are acquired and processed to reconstruct images of the features within the patient/object 118.

Source 112 is controlled by a system controller 124, which furnishes both power, and control signals for CT examination sequences, including acquisition of two-dimensional localizer or scout images used to identify an anatomy of interest within the patient/object for subsequent scan protocols. In the depicted embodiment, the system controller 124 controls the source 112 via an X-ray controller 126 which may be a component of the system controller 124. In such an embodiment, the X-ray controller 126 may be configured to provide power and timing signals to the X-ray source 112.

Moreover, the detector 122 is coupled to the system controller 124, which controls acquisition of the signals generated in the detector 122. In the depicted embodiment, the system controller 124 acquires the signals generated by the detector using a data acquisition system 128. The data acquisition system 128 receives data collected by readout electronics of the detector 122. The data acquisition system 128 may receive sampled analog signals from the detector 122 and convert the data to digital signals for subsequent processing by a processor 130 discussed below. Alternatively, in other embodiments the digital-to-analog conversion may be performed by circuitry provided on the detector 122 itself. The system controller 124 may also execute various signal processing and filtration functions with regard to the acquired image signals, such as for initial adjustment of dynamic ranges, interleaving of digital image data, and so forth.

In the embodiment illustrated in FIG. 2, system controller 124 is coupled to a rotational subsystem 132 and a linear positioning subsystem 134. The rotational subsystem 132 enables the X-ray source 112, collimator 114 and the detector 122 to be rotated one or multiple turns around the patient/object 118, such as rotated primarily in an x, y-plane about the patient. It should be noted that the rotational subsystem 132 might include a gantry upon which the respective X-ray emission and detection components are disposed. Thus, in such an embodiment, the system controller 124 may be utilized to operate the gantry.

The linear positioning subsystem 134 may enable the patient/object 118, or more specifically a table supporting the patient, to be displaced within the bore of the CT system 110, such as in the z-direction relative to rotation of the gantry. Thus, the table may be linearly moved (in a continuous or step-wise fashion) within the gantry to generate images of particular areas of the patient 118. In the depicted embodiment, the system controller 124 controls the movement of the rotational subsystem 132 and/or the linear positioning subsystem 134 via a motor controller 136.

In general, system controller 124 commands operation of the imaging system 110 (such as via the operation of the source 112, detector 122, and positioning systems described above) to execute examination protocols and to process acquired data. For example, the system controller 124, via the systems and controllers noted above, may rotate a gantry supporting the source 112 and detector 122 about a subject of interest so that X-ray attenuation data may be obtained at one or more views relative to the subject. In the present context, system controller 124 may also include signal processing circuitry, associated memory circuitry for storing programs and routines executed by the computer (such as routines for executing data completion processing or reconstruction techniques described herein), as well as configuration parameters, image data, and so forth.

In the depicted embodiment, the image signals acquired and processed by the system controller 124 are provided to a processing component 130 for reconstruction of images in accordance with the presently disclosed algorithms. The processing component 130 may be one or more general or application-specific microprocessors. The data collected by the data acquisition system 128 may be transmitted to the processing component 130 directly or after storage in a memory 138. Any type of memory suitable for storing data might be utilized by such an exemplary system 110. For example, the memory 138 may include one or more optical, magnetic, and/or solid state memory storage structures. Moreover, the memory 138 may be located at the acquisition system site and/or may include remote storage devices for storing data, processing parameters, and/or routines for projection data completion, as described below.

The processing component 130 may be configured to receive commands and scanning parameters from an operator via an operator workstation 140, typically equipped with a keyboard and/or other input devices. An operator may control the system 110 via the operator workstation 140. Thus, the operator may observe the reconstructed images and/or otherwise operate the system 110 using the operator workstation 140. For example, a display 142 coupled to the operator workstation 140 may be utilized to observe the reconstructed images and to control imaging. Additionally, the images may also be printed by a printer 144 which may be coupled to the operator workstation 140.

Further, the processing component 130 and operator workstation 140 may be coupled to other output devices, which may include standard or special purpose computer monitors and associated processing circuitry. One or more operator workstations 140 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 140 may also be coupled to a picture archiving and communications system (PACS) 146. PACS 146 may in turn be coupled to a remote client 148, radiology department information system (RIS), hospital information system (HIS) or to an internal or external network, so that others at different locations may gain access to the raw or processed image data.

As discussed herein, the present approach uses deep learning implemented as a trained neural network to estimate various types of missing projection data or data which may be used in tomographic reconstruction. The present approaches may also be used to generate corrected or adjusted data for regions where corruption or noise is known to exist in projection space. By way of example, in the context of a CT implementation the present deep learning approach may be used to estimate missing data directly in the projection data domain (also referred to as a sinogram in a CT context). A suitable subset of the available or known projection data serves as input of the neural network and an estimate of the missing projection data represents the desired output.

Figure 3:
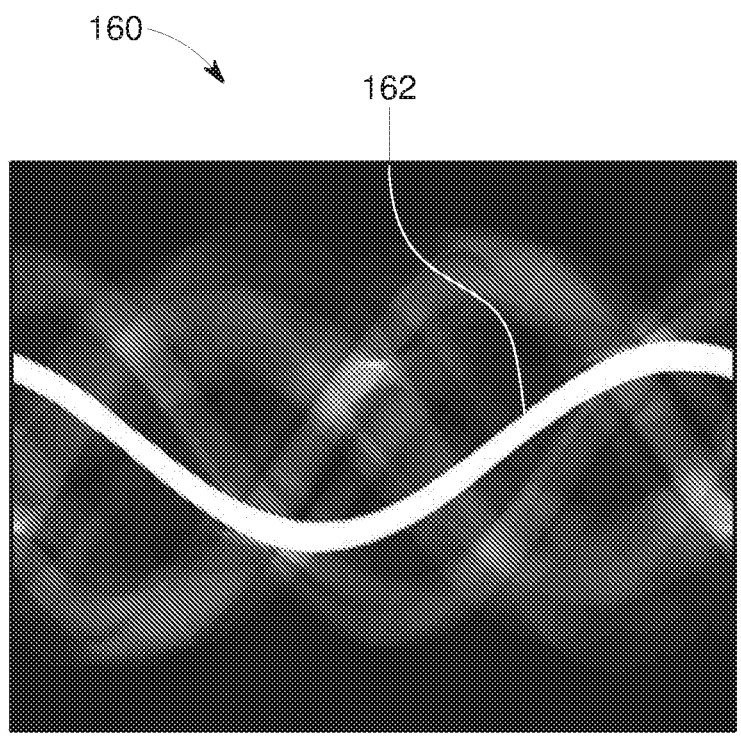
FIG. 3 depicts an example of a sinogram having missing data corresponding to an off-center metal object, thereby creating a region of missing or corrupted data, in accordance with aspects of the present disclosure.
Figure 4:
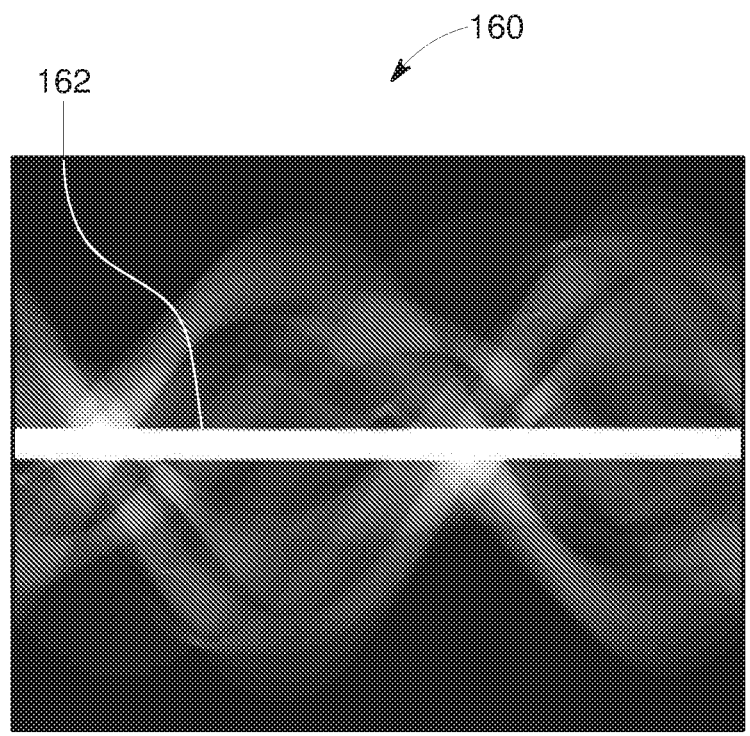
FIG. 4 depicts an example of a sinogram having missing data corresponding to a centered metal object or a missing detector region, in accordance with aspects of the present disclosure.

To illustrate the issues associated with missing projection data, various examples of sinograms exhibiting missing data are illustrated. For example, turning to FIGS. 3 and 4, the effects (i.e., "shadow") of a metal object (or other radiopaque material) located in the field-of-view (FOV) is illustrated in sinograms 160. This effect manifests as bands 162 of missing data in the sinograms 160, with the sinogram of FIG. 3 depicting an example where the radiopaque object is off-center within the FOV, thus tracing a sinusoidal form, while FIG. 4 depicts an example where the radiopaque object is centered within the FOV, thus tracing a straight line or band through the center of the sinogram. A similar situation with a missing straight band in the sinogram occurs when there is a physical gap in the detector or in cases where there are one or more corrupt detector cells. Note that although the bands of missing data are depicted as bands of constant (or nearly constant) width for the sake of simplicity and to demonstrate the concept in general, they may be varying in width (as a function of projection angle), for example for metal objects that do not have a circular cross-section. The methods for estimating the data in missing data regions disclosed herein extend to missing data regions of various shapes.

Figure 5:
FIG. 5 depicts an example of a view of a complete CT view or projection, in accordance with aspects of the present disclosure.
Figure 6:
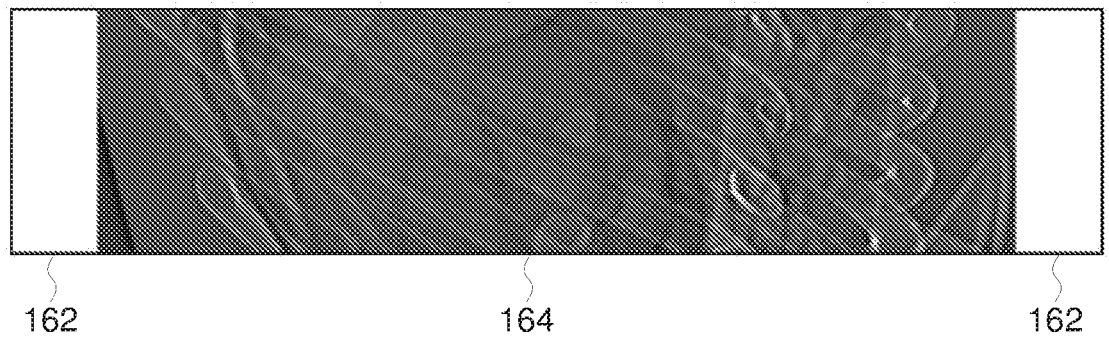
FIG. 6 depicts the CT view or projection of FIG. 5 truncated in a transaxial direction, in accordance with aspects of the present disclosure.
Figure 7:
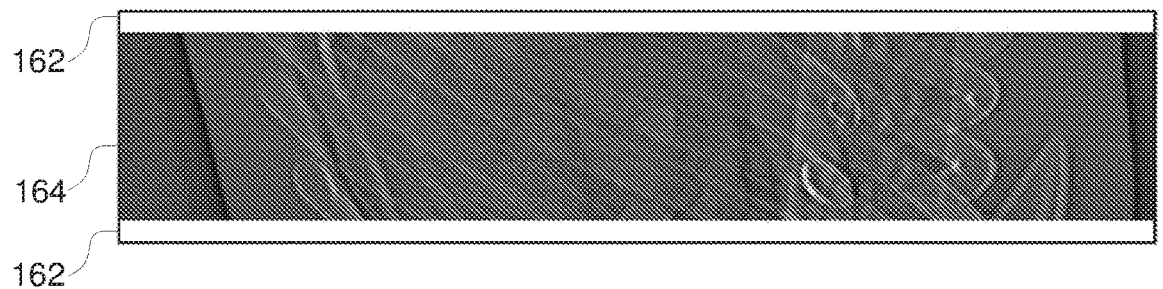
FIG. 7 depicts the CT view or projection of FIG. 5 truncated in a longitudinal direction, in accordance with aspects of the present disclosure.
Figure 8:
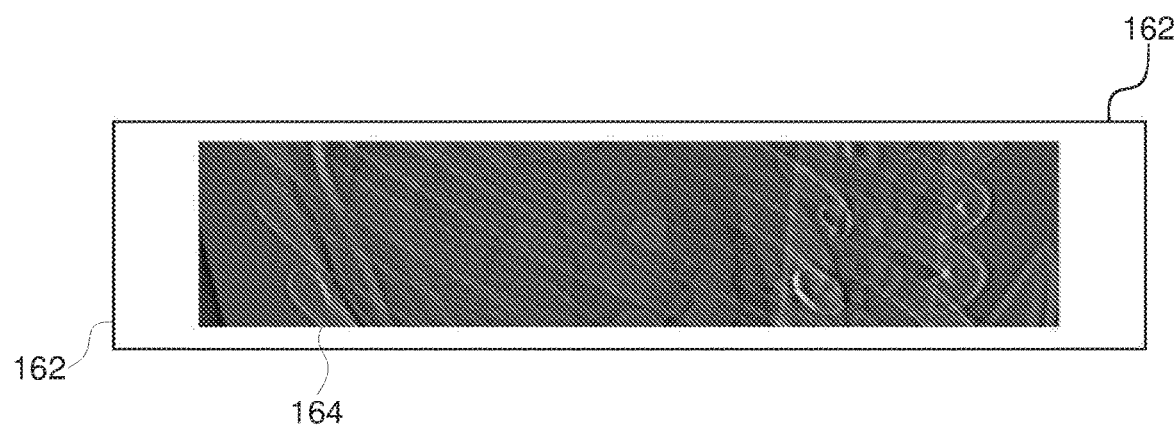
FIG. 8 depicts the CT view or projection of FIG. 5 truncated in both transaxial and longitudinal directions, in accordance with aspects of the present disclosure.

Similarly, FIGS. 5-8 depict examples of different types of data truncation (FIGS. 6-8), in comparison to a reference view of a corresponding complete CT view or projection 166 (as shown in FIG. 5). Data truncation (e.g., a truncated sinogram) may result when the detector is too small in a given dimension or dimensions (e.g., transaxial direction or longitudinal dimension) to measure the entire projection of the object. In such an example data may be missing in one or more bands 162 with respect to the truncated CT view or projection 164. Depending on the characteristics of the imaged object and its position relative to the rotational axis of the imaging system, data may be missing due to truncation only for a part of the scan (i.e., in an angular range that does no span the entire horizontal length of a sinogram), and the missing data regions may not be symmetric on both sides of the detector array. However, for simplicity, symmetric examples are shown in FIGS. 6-8. In these examples, FIG. 6 depicts an example, of a truncated CT view or projection 164 that is truncated transaxially; FIG. 7 depicts an example, of a truncated CT view or projection 164 that is truncated longitudinally; and FIG. 8 depicts an example, of a truncated CT view or projection 164 that is truncated transaxially and longitudinally.

With respect to missing data regions 162, as shown in FIGS. 3-5, the presence, extent, and boundaries of such regions may be determined using one or more techniques or combinations of techniques. By way of example, a missing data region 162 may be determined using one or more of: (1) thresholding or segmentation directly in the projection domain; (2) an initial image reconstruction, followed by thresholding or segmentation in the image domain, followed by re-projection, followed by thresholding or masking; (3) a bad pixel map based on detector calibration experiments; (4) a known detector geometry with gaps between detector modules or panels; or (5) adding a fixed number of additional detector rows or columns to estimated truncated projection data. In one embodiment, regions of corrupted data may be identified or estimated by an evaluation of the local projection image quality, which itself may use a deep learning approach (or other approach known in the art) to estimate the local "quality" of the acquired projection data. Combinations of these and other methods for identifying regions of missing/corrupted data in the projection domain may also be used.

Figure 9:
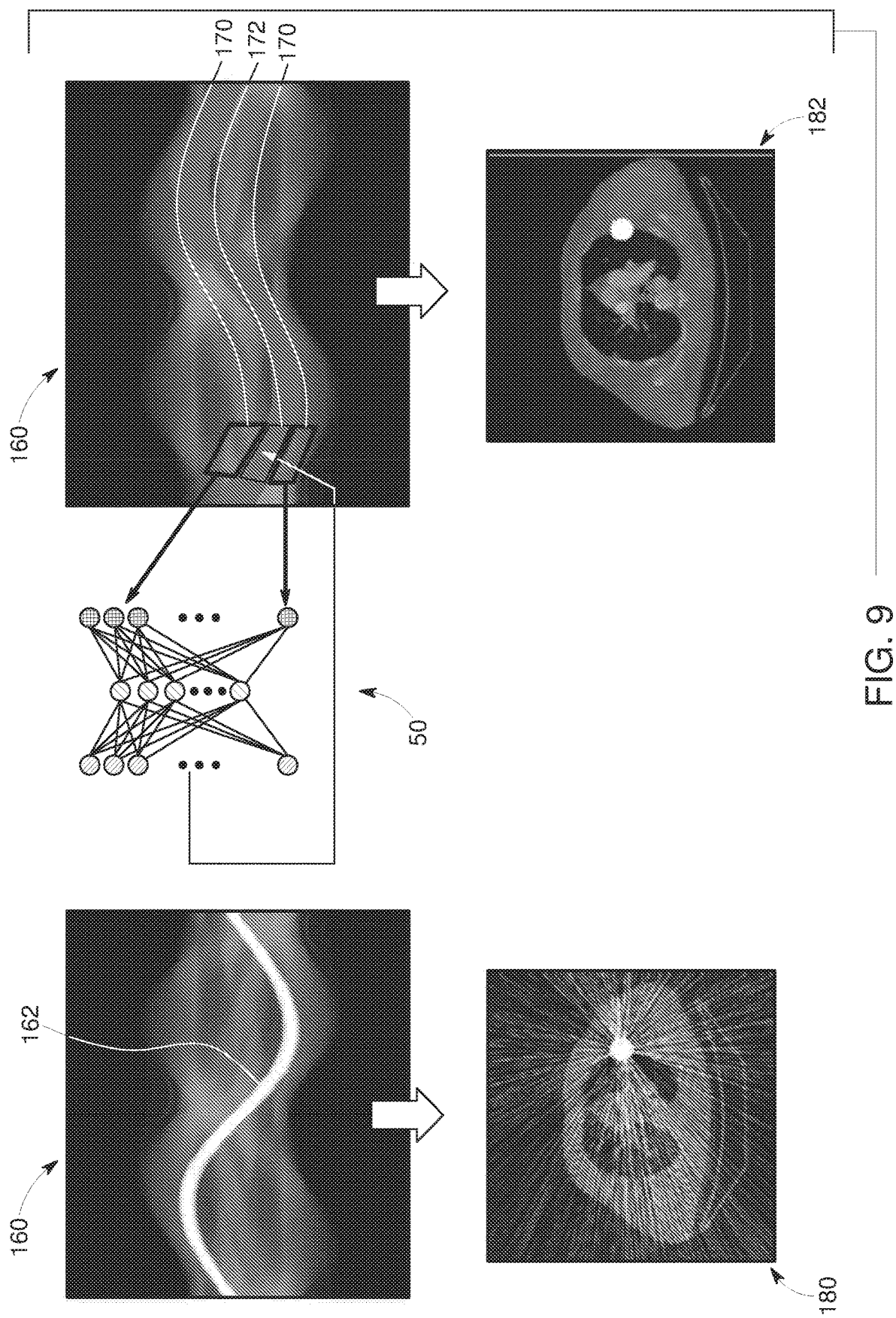
FIG. 9 depicts a visual representation of a process flow by which a trained neural network is used to estimate sinogram data in a missing data region, in accordance with aspects of the present disclosure.

Standard interpolation and extrapolation methods have generally not been satisfactory in providing estimates of the missing data 162, such as in such cases described above. In contrast, the present approach instead employs deep learning implemented as a trained neural network 50 to estimate the missing data 162. This is conceptually illustrated in FIG. 9. On the left-side of the figure, a sinogram 160 having missing data 162 is illustrated. If reconstructed, this sinogram will yield a reconstructed image 180 having metal artifacts, here evident as a "star-burst" type pattern centered around a radiopaque (e.g., metal) object in the FOV. Conversely, on the right-side of FIG. 9, the same sinogram is depicted as undergoing a missing data estimation or replacement using a trained neural network 50. In this example, the adjacent areas 170 to regions of missing data 162 are used as inputs to the trained neural network 50 to obtain an output 172 of the neural network 50 that is an estimate of the missing projection values. The sinogram 160 may be reconstructed with the estimated missing values to generate a reconstructed image 182 that does not exhibit the same type of streaking artifacts as the image 180 where no estimation of the missing data 162 was performed.

Figure 10:
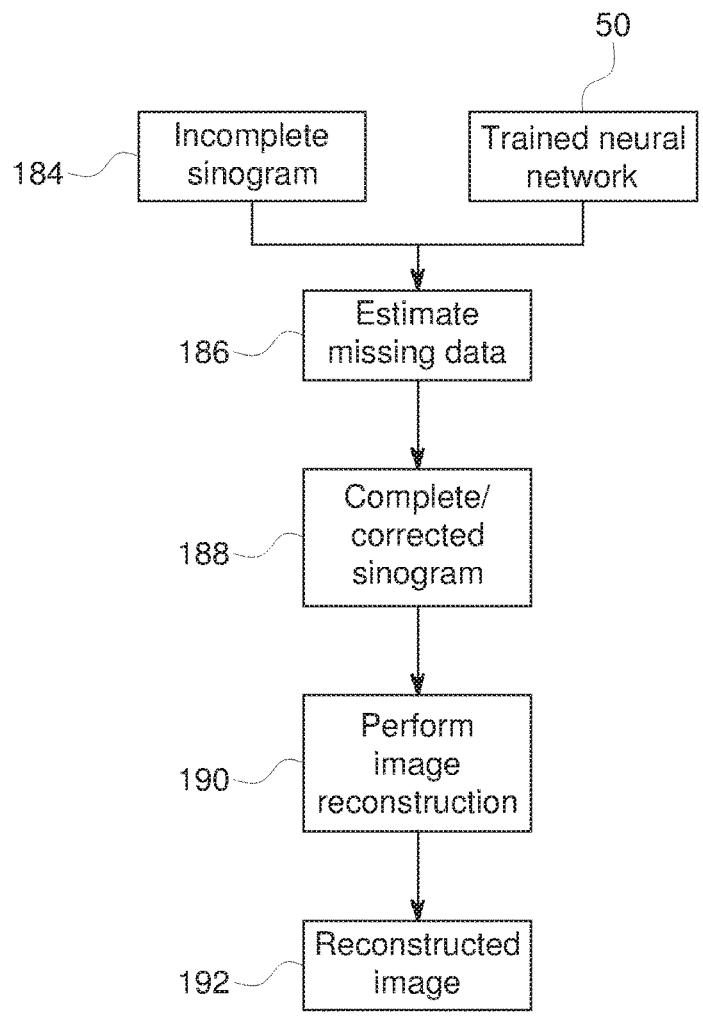
FIG. 10 depicts a process flow diagram of steps for estimating sinogram data, in accordance with aspects of the present disclosure.

This is further illustrated in FIG. 10, which depicts a process flow diagram of the steps described above. In this example, an incomplete sinogram 184 is initially provided, all or part of which is used as inputs to a trained neural network 50. The neural network 50 is used to estimate (step 186) projection data that is missing (or corrupted or otherwise not suitable) from the sinogram 184. The estimated data is used to generate a complete or corrected sinogram 188. The complete or corrected sinogram 188 may then be reconstructed (step 190) using a suitable reconstruction approach to generate a reconstructed image 192.

With respect to the neural network 50 used in such an approach, such a neural network may be trained using a number (e.g., tens, hundreds, or thousands) of training datasets where the target output of the neural network 50 is known. After the network 50 is trained it can be applied to test datasets to see if the output of the network meets expectations on datasets that were not used for training.

One approach for defining a training dataset is to start from datasets (e.g., sinograms) with no missing data (which may be generated using actual measured data and/or by simulation) and to omit a portion of the data (which is now considered "missing") for the purpose of training the network 50. Thus, the true value of the "missing" (i.e., removed or withheld) data are known. The neural network 50 is then trained such that its output closely resembles the data that was left out. The same approach can be used for testing the neural network. When successful, the output of the neural network 50 will closely match the missing data in the test datasets. Thus, during training data may consist of unaltered data where some region in the projection (sinogram) data is labeled as missing, and the desired output consists of the un-altered sinogram data corresponding to the missing data. The training data may in this manner contain structures that in an actual missing data instance would not be available.

In some cases, such as with patient data, no "ground truth" dataset may be available, training in such a scenario may instead be based on image quality metrics (e.g., using calculated image quality measures, observer models, or human observers). In another case, patient data without "missing data" limitations may be utilized as training data. For example, in the context of hip implants (which, when present, may lead to missing data regions in the projection data), pre-implant scans (which do not exhibit missing data problems) may be utilized as training data. In some instances it may be desirable to not only "learn" generic data estimation approaches which are widely applicable to a variety of imaged objects/anatomies, but to train the network for a specific clinical application (i.e., application-specific trained neural networks). In the example of hip implants, the location of the hip implant relative to other anatomical structures is generally well-known, and in such an instance a network that is specifically trained for this application may be optimized to recover the missing data with characteristics that are specific to the imaged hip-region of the patient. Similarly, a neural network may be trained to be anatomy-specific so as to address missing data or data corruption issues common to particular anatomic regions (such as by training using data sets generated for or specific to a particular anatomic context). Anatomic- and application-specific factors may be combined, such as to train a neural network, or use a trained neural network, specific to a particular application and anatomy (e.g., hip implants). A neural network may also be trained to be task-specific, such as to address missing data or data corruption specific to certain types of errors (e.g., data truncation, metal artifacts, and so forth), such as by training using data sets generated for or specific to a missing data or data corruption condition. In another scenario, some portion of a two-dimensional (2D) or 3D region of the patient image may be replaced by a "smooth" interpolation, (i.e., this region does not contain any image structure), before simulating projection data from the patient data. In the example of the hip implants, the implants themselves will be uniform and they will take the place of any anatomical structures that were present in that anatomical location before. Therefore, training the network with data where the corresponding image structure has been "taken out" represents a suitable dataset for training.

With the preceding in mind a trained neural network 50 may be used in various ways to provide data estimation. Various implementations and variations are discussed below to provide useful examples and further context.

Figure 11:
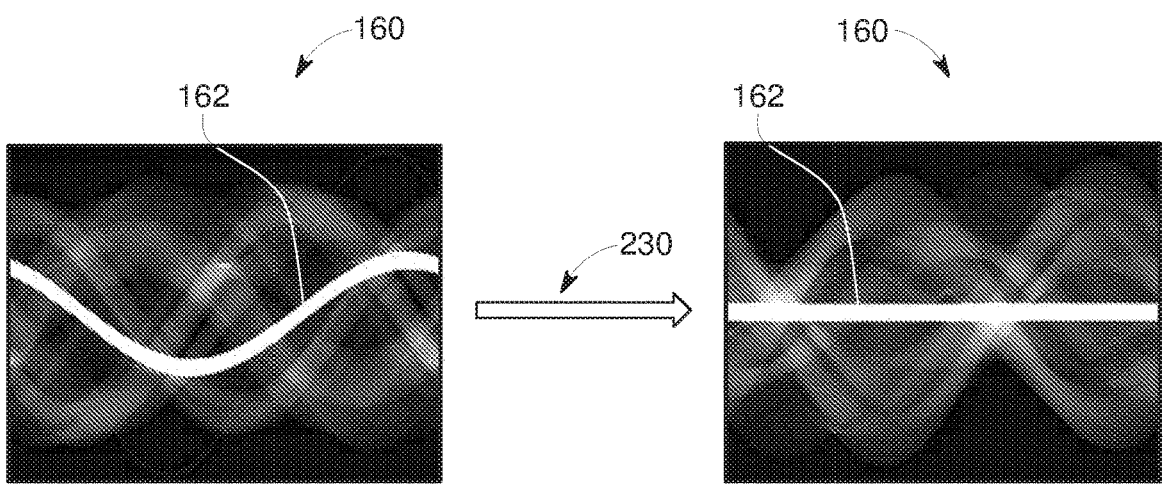
FIG. 11 depicts a rebinning operation, in accordance with aspects of the present disclosure.

Prior to discussing implementations of missing data estimation using deep learning, it may be noted that many such estimations, particularly those performed with respect to metal or radiopaque objects in the field of view, may benefit from a re-binning of the sinogram data, as shown in FIG. 11, prior to the estimation of the missing data 162. In particular, the geometric implications are simplified if, before the estimation steps, a re-binning (step 230) of the data to correspond to a parallel beam geometry is performed. Such a re-binning may be combined with or performed with a shift such that the missing data region 162 is centered in the sinogram 160. As a consequence, the trace of the missing data region 162 is represented as a straight line (or band).

In this manner, acquired data may be re-binned to represent data acquired using a parallel beam acquisition, where the missing data region 162 is at the center of the field of view. By placing the metal (or other radiopaque) object (after re-binning) in a centered location, the geometry of patches and traces relatively to the trace of the metal region is straightforward since the missing data region 162 traces a central straight line/band through the sinogram 160.

With the preceding in mind, in one example of deep learning based missing data estimation, a patch-based interpolation may be performed using a trained neural network 50.

In this approach the data at a pixel or small region/patch 200 in the missing data region 162 is estimated based on a neighboring patch 202 of data in the region for which data is available. The data from the patch 202 for which data is available is, in one implementation, selected close to the boundary of the missing data region 162, and close to the patch 200 to be estimated.

Figure 12:
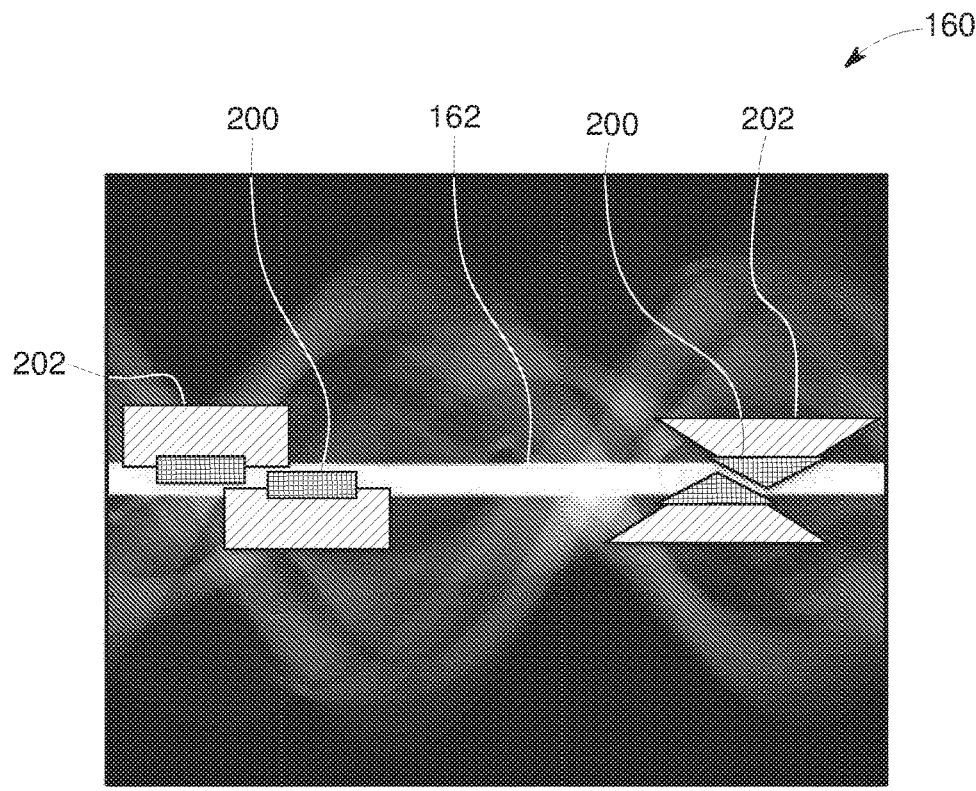
FIG. 12 depicts a one-sided patch-based estimation operation, in accordance with aspects of the present disclosure.
Figure 13:
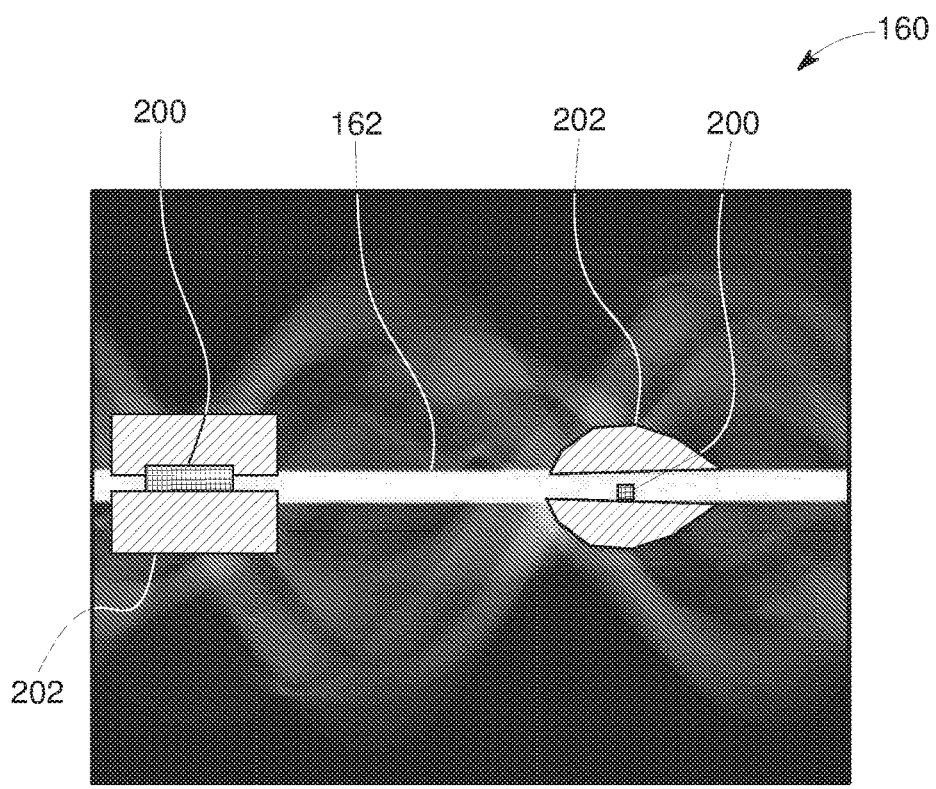
FIG. 13 depicts a two-sided patch-based estimation operation, in accordance with aspects of the present disclosure.

This approach is illustrated in FIGS. 12 and 13, in which the figures show examples for a metal artifact reduction problem. The patch regions 200 are examples of sinogram values or patches being estimated and the known region 202 are the data used as the input to the neural network 50 to estimate these respective missing data patches 200. Similar approaches can be used for other types of missing data such as bad pixel correction or truncation.

In these examples, the patch 202 that represents the input data may be a rectangular shape, or a section of a "wedge" shape, which may be better adapted to the sinusoid traces of different structures in the sinogram. Other patch shapes may be selected as well. Generally the input patch 202 represents a larger angular range (i.e., the input patches are generally "wider" in the angular i.e., horizontal, direction) than the patch 200 to be estimated, and is selected based on representing a region on the detector adjacent to the missing data region 162. If only data on one side of the missing data region 162 is used as input for the estimation of a given patch, it may be referred to as "one-sided" estimation (examples of which are shown in FIG. 12). If data from both sides of the missing data 162 region is used, this may be referred to as "two-sided" estimation (examples of which are shown in FIG. 13).

By using this kind of approach, separate patches 200 of missing data may be estimated independently, such that all estimated patches of data cover a part of, or the entire, missing data region. The patches 200 where data is estimated may be selected to be overlapping, which may then utilize a separate smoothing/consolidation step to combine the estimation results 200 in overlapping regions into a single smooth overall interpolation of the data in the missing data region 162.

Figure 14:
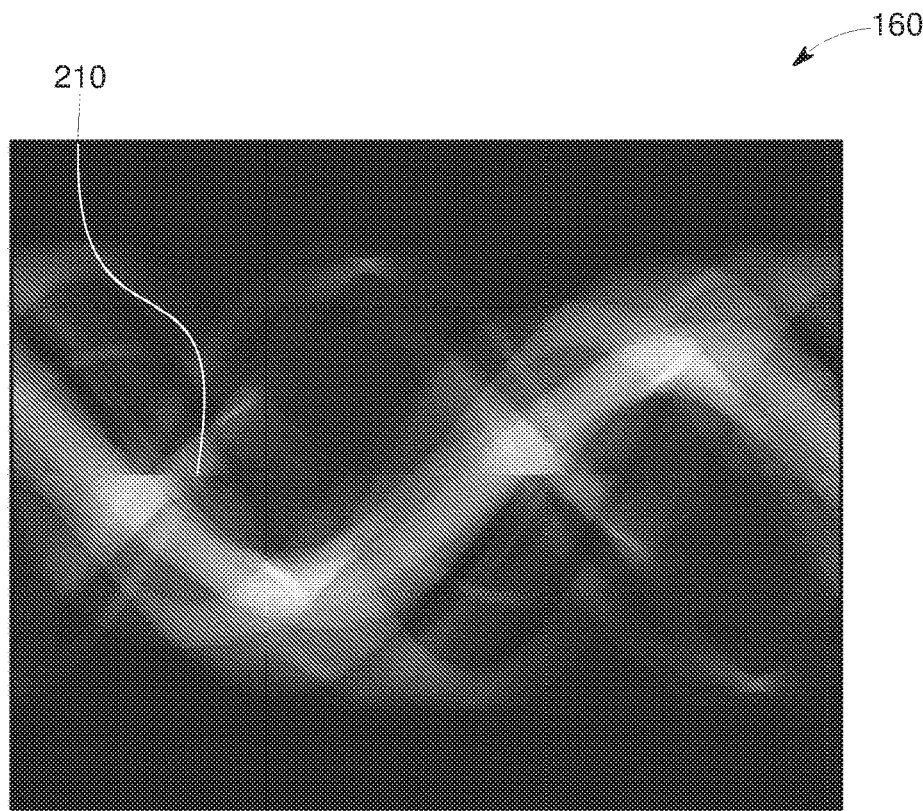
FIG. 14 depicts an example of a result from a projection data estimation operation, in accordance with aspects of the present disclosure.

Turning to FIG. 14, an example of a result is depicted. Small rectangular patches are estimated independently and separately, using a one-sided estimation based on rectangular patches in the adjacent region where data is available. As a result, there is a visible discontinuity 210 in the interpolated data where the estimates from both sides meet. This issue can be addressed with a suitable step in which overlapping patches are combined. By using, for example, a suitably weighted smooth transition between overlapping patches, the corresponding information may be combined into a smooth interpolated region. For example, the data at each pixel in the sinogram may be selected as a weighted average of several patches at that location (i.e., in an overlap region where multiple estimates exist), where the weights are chosen such as to ensure a smooth transition between patches. Alternatively, the estimated overlapping patches may be combined using another neural network processing step (or one or more additional layers of the existing neural network 50).

Figure 15:
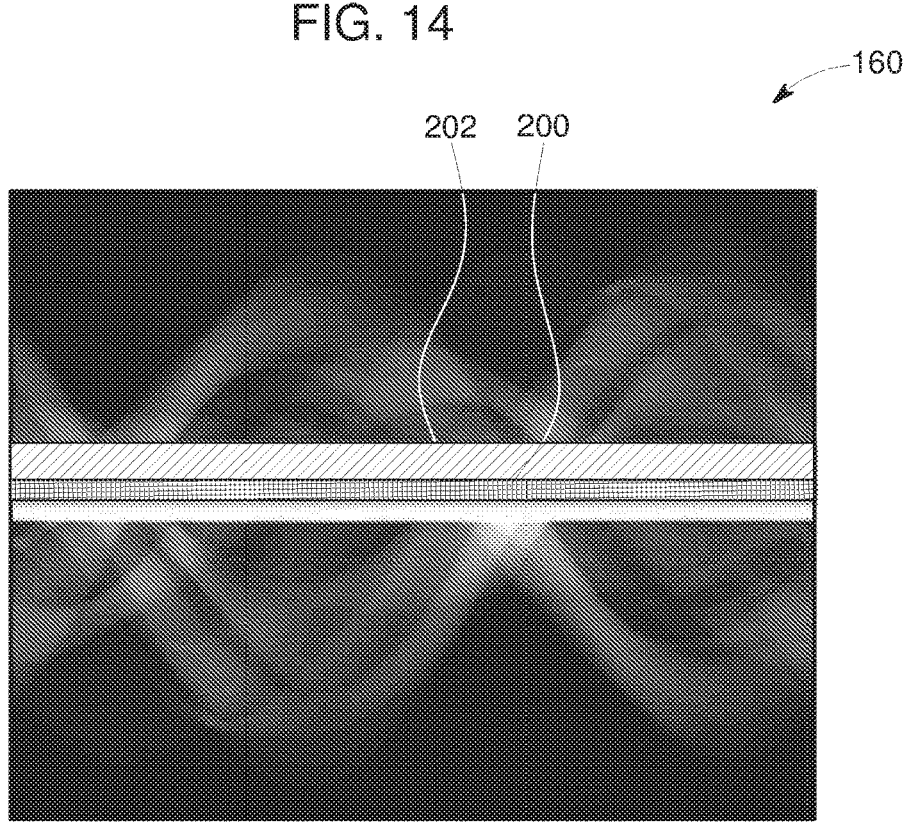
FIG. 15 depicts a trace-based estimation operation, in accordance with aspects of the present disclosure.

In a further example of deep learning based interpolation, in one implementation a trace-based interpolation is performed, where a sinogram trace is understood to be a portion of a sinogram (typically of sinusoidal shape) that corresponds to a specific region in image space. For instance, a region corresponding to metal object in image space will result in shadowing or data corruption in a corresponding sinusoidal trace in the sinogram. In such an embodiment one or more traces of the missing data region 162 (e.g., a sinusoidal curve or a straight line through the missing data region after suitable re-binning of the data, as discussed below) is estimated based on two or more traces (e.g., lines) within the data available region, as show schematically in FIG. 15.

Generally, the input data 202 will be selected to correspond to the traces closest to the missing data region. For example, the trace closest to the missing data region corresponds to the sequence of rays that are tangential to the (assumed here to be circular-shaped) missing data region. A network may be trained such that it produces estimates of the projection data in the missing data trace 200, when using the input data 200. Since the traces each represent 360 degrees of data, the data within each trace is periodic—therefore it may be advantageous to utilize a Fourier space representation of the data at some stage in the processing.

As may be appreciated hybrid approaches based on both the patch-based and trace-based approaches may be employed. In the limit, both approaches may be considered equivalent in the sense that in both scenarios all available data may be used as input, and all of the missing data is considered as the output. However, when the dimensionality of either input data or output data (or both) is becoming too large, then processing and training may become difficult and/or slow.

Figure 16:
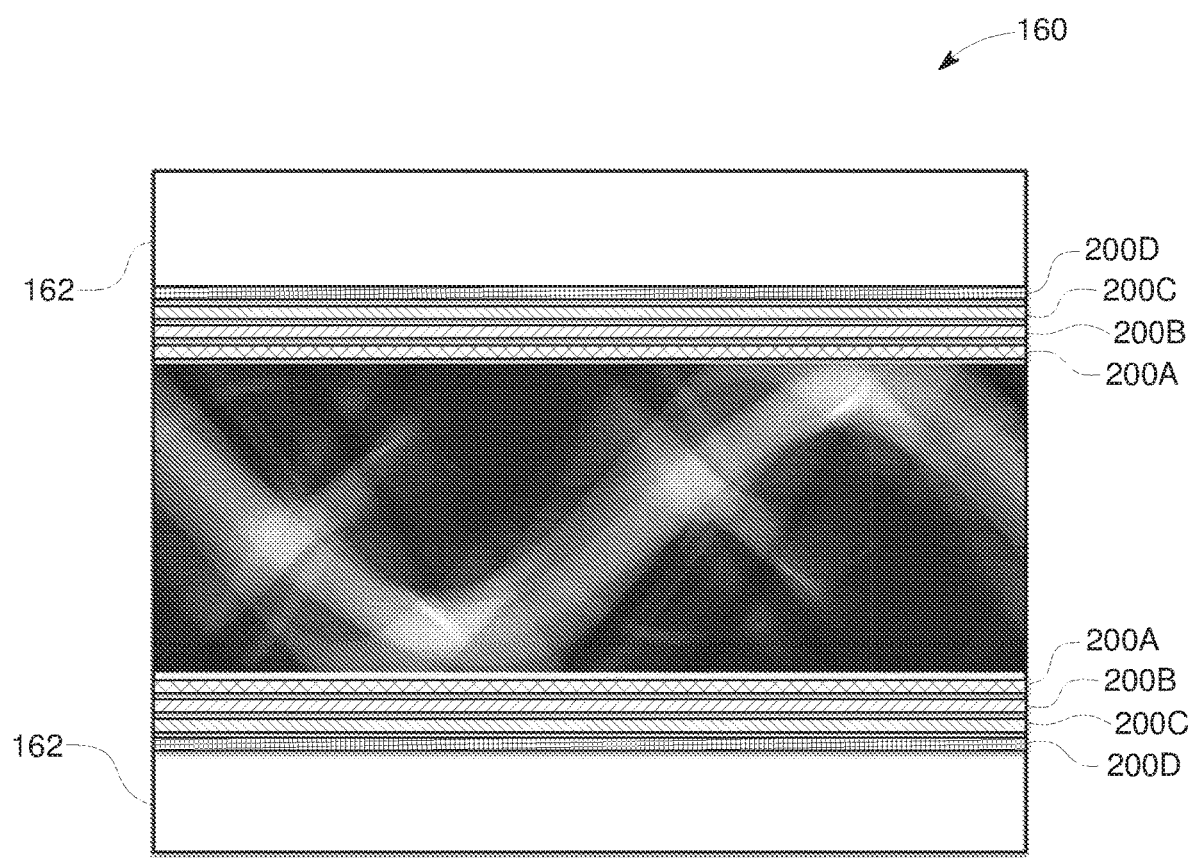
FIG. 16 depicts a recursive estimation operation, in accordance with aspects of the present disclosure.

While the preceding outline deep learning based estimation approaches, a further consideration is that some or all of these approaches may be implemented in a recursive manner. For example, a recursive estimation may be performed, where initially only a patch or region 200 of data that is close to the boundary of the missing data region 162 is estimated using one or more trained neural networks 50. In one example this may consist of estimating the missing data layer by layer outward from the known data. Once a single "layer" is estimated (either by estimating it as one single data vector, or by estimating sections of it and later combining), the next layer may be estimated using the previously estimated layer as part of the "known" data until the whole missing data region 162 is filled. This strategy may be applicable to both the patch-based and the trace-based estimation. An example for transaxial truncation is shown in FIG. 16, where traces 220A are first estimated. Then the trained neural network(s) 50 is subsequently applied to estimate traces 200B and traces 200A can become part of the input data as they are no longer missing, and so forth with respect to traces 200C and 200D.

Figure 17:
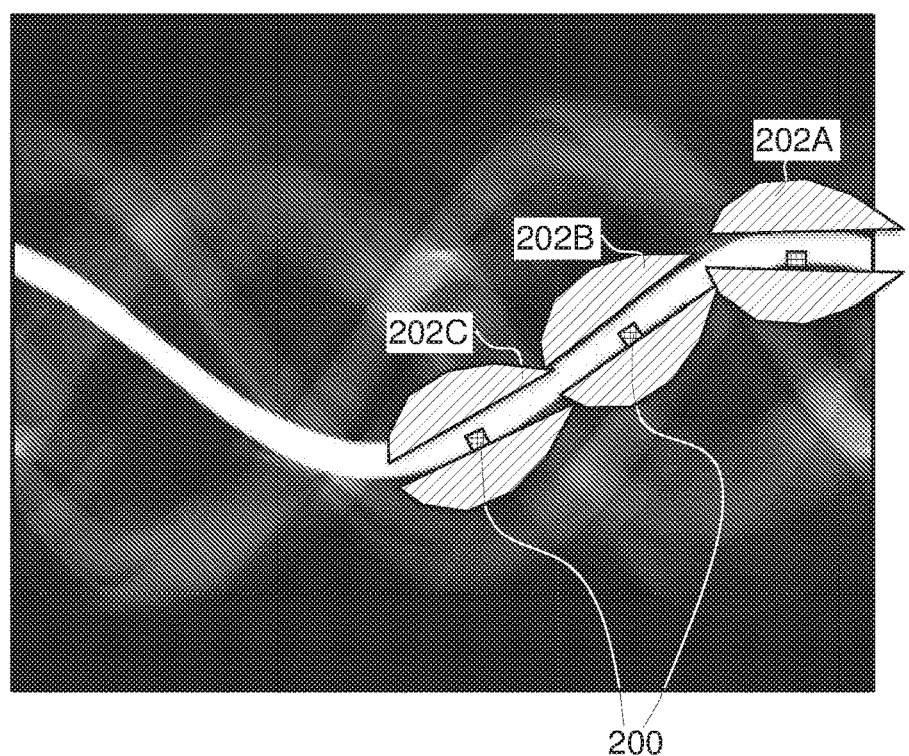
FIG. 17 depicts a spatially variant estimation operation, in accordance with aspects of the present disclosure.
Figure 18:
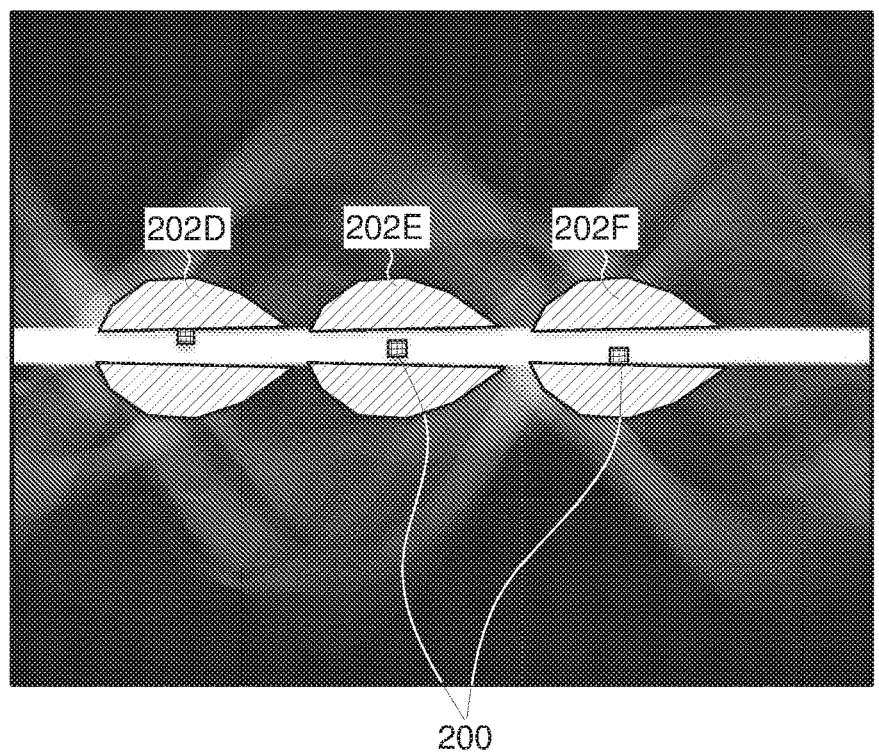
FIG. 18 depicts an alternative spatially variant estimation operation, in accordance with aspects of the present disclosure.

It may also be noted that, while the preceding example(s) suggest the use of a single (i.e., spatially invariant) trained neural network 50 used to estimate missing sinogram data, in practice different deep learning networks may be employed that are trained to the patterns or spatial arrangements present in the sinogram at a particular instance (i.e., spatially variant deep learning networks). By way of example, depending on the location of the missing data (i.e., the output of the network) and the available data (i.e., the input to the network), a differently-trained deep learning network may be suitable for different spatial circumstances (e.g., for different structures and/or different parameters). For instance, in the case of a fan-beam or cone-beam sinogram where re-binning has not been performed, different locations in sinogram space have different geometrical properties, as illustrated in FIG. 17 where known regions 202A, 202B, and 202C correspond to different geometric regions of the sinogram used in a two-sided interpolation of unknown patches 200. Due to the geometric differences between regions, differently trained deep learning networks may be employed for these different regions 202A, 202B and 202C. Similarly, as shown in FIG. 18, another example of a situation where differently trained deep learning networks may be desirable is where the distance and/or position of the patches 200 being estimated vary with respect to the known regions used as inputs 202D, 202E, and 202F. That is, deep learning neural networks 50 may be trained or specialized based on spatial location with respect to a region of missing data and/or based on the relative location, distance, and/or orientation of the estimated patch 200 relative to the input data 202 such that different deep learning networks may be used based on the particular circumstances of the missing data to be estimated.

Technical effects of the invention include the use of trained neural networks to estimate various types of missing projection (or other unreconstructed) data. The neural networks can be trained using projection or other data where a portion of the data is defined as the missing data to be estimated and the remaining data is the available data that can be used as the input to the network. Similarly, the present approach may also be employed to replace or correct corrupted or erroneous projection data (as opposed to estimating missing projection data). For example, more general data errors (such as due to beam hardening, scatter, noise, and so forth) may be addressed by this approach using a trained neural network and the methodology generally described herein. In such instances, instead of estimating missing projection data, one or more correction terms may be estimated that may be employed to correct the incorrect data. In this case the corrupted data itself may serve as an additional input to the network.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for estimating missing data for use in a tomographic reconstruction, comprising:
    acquiring or accessing a set of scan data, wherein the set of scan data has one or more regions of incomplete or unsuitable data;
    processing the set of scan data using one or more trained neural networks;
    performing a re-binning operation on the set of scan data prior to processing the set of scan data using the one or more trained neural networks;
    generating an estimated data set for each region of incomplete or unsuitable data using the one or more trained neural networks, wherein the set of scan data in combination with the estimated data sets correspond to a corrected set of scan data; and performing a tomographic reconstruction of the corrected set of scan data to generate one or more reconstructed images.

2. The method of claim 1, wherein the set of scan data comprises one or more sinograms.

3. The method of claim 1, wherein the one or more trained neural networks perform one or more of a one-sided patch-based interpolation, a two-sided patch-based interpolation, or a trace-based interpolation to generate the estimated data sets using one or more regions of suitable data from the set of scan data.

4. The method of claim 1, further comprising:
performing a smoothing operation on the estimated data sets and the set of scan data as part of forming the corrected set of scan data.

5. The method of claim 1, wherein processing the set of scan data using the one or more trained neural networks comprises recursively processing the set of scan data such that estimated data sets of one processing step comprise a portion of the input in a subsequent processing step.

6. The method of claim 1, wherein the one or more trained neural networks comprise at least two trained neural networks that are not spatially invariant.

7. The method of claim 1, wherein the one or more trained neural networks comprise a plurality of trained neural networks that vary based on the geometry of the regions of incomplete or unsuitable data for which they are trained.

8. The method of claim 1, wherein the one or more trained neural networks comprise a plurality of trained neural networks that vary based on the distance or location of a patch of estimated data which they are trained to output.

9. The method of claim 1, wherein the one or more trained neural networks estimate residual image data or other processed or filtered image data.

10. The method of claim 1, wherein a respective estimated data set comprises one of a single projection data number, a projection data patch, or a trace of projection data.

11. The method of claim 1, further comprising:
performing a pre-processing step on the set of scan data prior to processing using the one or more trained neural networks; and
performing a post-processing step that is the inverse of the pre-processing step on the estimated data set.

12. The method of claim 11, wherein the pre-processing step comprises a high-pass filter operation and the post-processing step comprises a low-pass filtering operation inverse to the high-pass filter operation.

13. The method of claim 1, further comprising:
performing a normalization step on the set of scan data by dividing or subtracting a reprojected sinogram prior to processing using the one or more trained neural networks; and
reversing the normalization step by adding or multiplying by the reprojected sinogram.

14. The method of claim 1, further comprising:
providing weight data to the one or more trained neural networks in addition to the set of scan data, wherein the weight data correspond to a measure of confidence or reliability of the set of scan data.

15. The method of claim 14, wherein the weight data comprises a weight element for each corresponding element in the set of scan data and higher weights correspond to greater confidence.

16. An image processing system comprising:
a processor configured to execute one or more stored processor-executable routines; and
a memory storing the one or more executable-routines, wherein the one or more executable routines, when executed by the processor, cause acts to be performed comprising:
acquiring or accessing a set of scan data, wherein the set of scan data has one or more regions of incomplete or unsuitable data;
processing the set of scan data using one or more trained neural networks;
performing a re-binning operation on the set of scan data prior to processing the set of scan data using the one or more trained neural networks;
generating an estimated data set for each region of incomplete or unsuitable data using the one or more trained neural networks, wherein the set of scan data in combination with the estimated data sets correspond to a corrected set of scan data; and
performing a tomographic reconstruction of the corrected set of scan data to generate one or more reconstructed images.

17. The imaging processing system of claim 16, wherein the one or more trained neural networks perform one or more of a one-sided patch-based interpolation, a two-sided patch-based interpolation, or a trace-based interpolation to generate the estimated data sets using one or more regions of suitable data from the set of scan data.

* * * * *